United States Patent [19]

Haruki et al.

[11] 3,932,264
[45] Jan. 13, 1976

[54] ELECTROPHORETIC MEASUREMENT SYSTEM INCLUDING MEANS FOR DETERMINING ZONE BOUNDRIES

[75] Inventors: Tatsuro Haruki, Nishinomiya; Junichi Akiyama, Kyoto, both of Japan

[73] Assignee: Shimadzu Seisakusho Ltd., Kyoto, Japan

[22] Filed: Nov. 12, 1973

[21] Appl. No.: 414,970

[52] U.S. Cl............ 204/299; 204/180 G; 204/180 R; 204/195
[51] Int. Cl.$^2$.......................................... B01K 5/00
[58] Field of Search............ 204/180 R, 180 G, 299, 204/195

[56] References Cited
UNITED STATES PATENTS

| | | | |
|---|---|---|---|
| 3,594,294 | 7/1971 | Pretorius et al. | 204/180 G |
| 3,725,232 | 4/1973 | Pretorius et al. | 204/180 G |
| 3,759,816 | 9/1973 | Pretorius et al. | 204/299 |
| 3,788,969 | 1/1974 | DiStefano et al. | 204/299 |

OTHER PUBLICATIONS

Duckworth, "Electricity and Magnetism," Holt, Rinehart, and Winston, N.Y., 1961, pp. 159 & 160.

*Primary Examiner*—John H. Mack
*Assistant Examiner*—A. C. Prescott
*Attorney, Agent, or Firm*—George B. Oujevolk

[57] ABSTRACT

An electrophoretic measurement system for isotachophoresis includes a potential gradient detector, an impedance converter, a voltage to frequency converter, a signal transmission system composed of, for example, electromagnetic wave transmitter means and its receiver spaced therefrom, frequency to voltage converter means, in series connection. This arrangement facilitates insulation of the sensing electrodes of the detector from the ground and prevents a formation of bubbles and deposits on the electrodes, so that the electrophoresis processes are performed under stable condition and high resolution and high sensitivity are obtained. Besides a higher migration current can be used to shorten analysis time.

14 Claims, 15 Drawing Figures

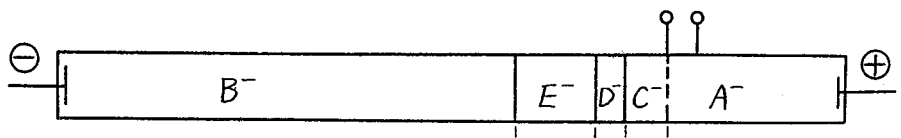
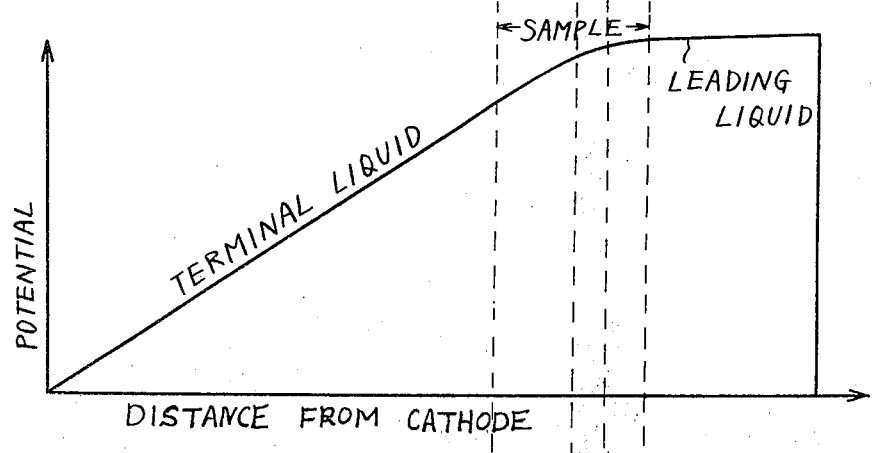
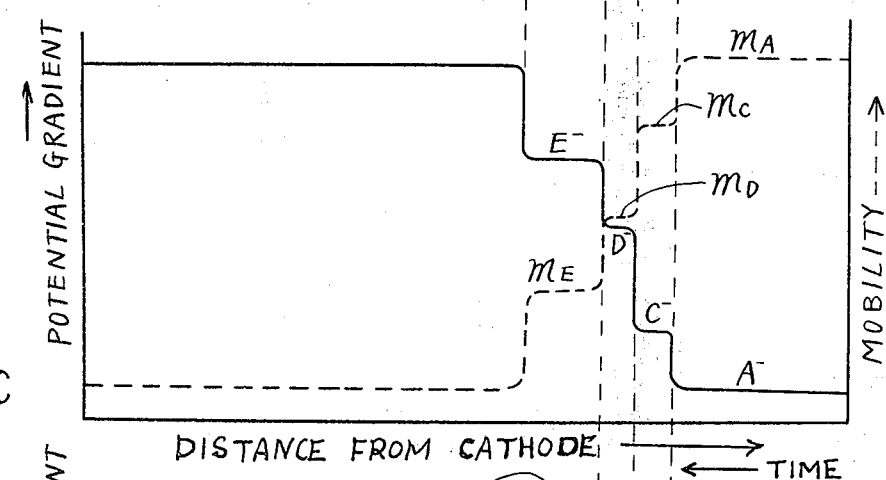
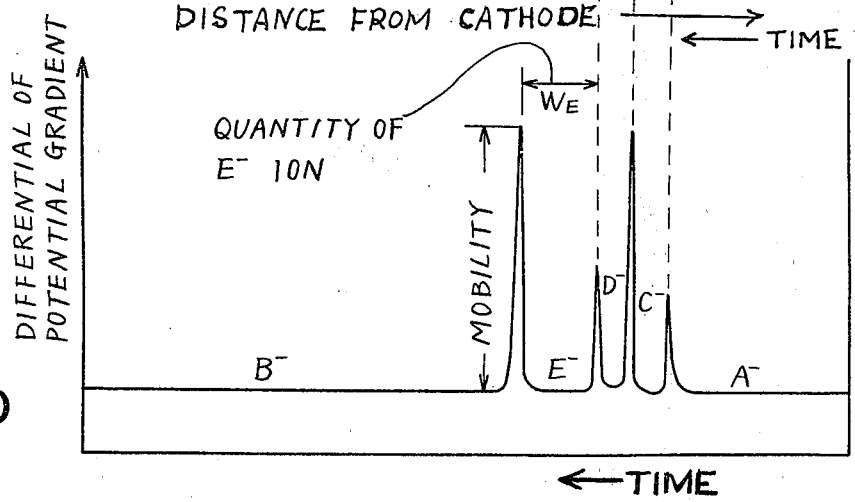

ELECTROPHORETIC MEASUREMENT SYSTEM INCLUDING MEANS FOR DETERMINING ZONE BOUNDRIES

BACKGROUND OF THE INVENTION

The present invention relates to an electrophoretic measurement system, and more particularly to a new system for measuring zone boundaries in an isotachophoresis system.

BRIEF DESCRIPTION OF THE PRIOR ART

In isotachophoresis, a potential difference is applied across a capillary tube containing a leading electrolyte and a terminal electrolyte holding a sample solution which is generally interposed at or near the boundary of the electrolytes. The sample ions are e.g. anions, the leading electrolyte contains a single sort of anions and their mobility is higher than that of sample ions; the terminal electrolyte also contains a single sort of anions but with a lower mobility than that of sample ions. Then the anions within the sample move towards the anode between the anions of the leading electrolyte and the anions of the terminal electrolyte.

The unknown anions in the sample will be separated slowly into distinct layers in the order of their mobilities. The boundaries formed between each layer are detected by a detector.

Heretofore various detectors for capillary-type isotachophoretic system have been proposed, but none of them has been put to practical use.

The most important reason for this may be the fact that there has not been developed a method that can detect zone boundaries in a capillary tube with a high resolution for most types of samples. A thermometric detector has not been found satisfactory due to its rather low resolution. An ultra-violet detector has not been used as a universal detector because of the existence of many compounds that do not absorb UV. A potential gradient detector and a conductivity detector have also been developed as promising high resolution detectors. These detectors, however, have not yet been put to practical use, because electrochemical bubbles and deposits produced on the sensing electrodes tend to impede the smooth performance of isotachophoresis.

OBJECTS OF THE INVENTION

Accordingly, the general object of the invention is to provide an improved electrophoresis analyzer which overcomes to a high degree many of the disadvantage of the prior art.

Another object of the invention is to provide an improved electrophoresis analyzer with stable operation without the formation of bubbles and deposits on the sensing electrodes.

A further object of the invention is to provide an improved electrophoresis analyzer having a good resolution and sensitivity.

A still further object of the invention is to provide an improved electrophoresis analyzer capable of shortening the time for analysis.

These and other objects, features and advantages of the present invention will become more apparent upon a reading of the following detailed specification and drawings, wherein:

BRIEF DESCRIPTION OF THE DRAWINGS

FIG. 6A to FIG. 6D illustrate the operation of the electrophoresis process in the present invention.

DETAILED DESCRIPTION

In accordance with the present invention, high resolution high sensitivity and shortening of time are achieved in an electrophoresis analyzer, by preventing bubble formation on the sensing electrodes.

Figure 1:
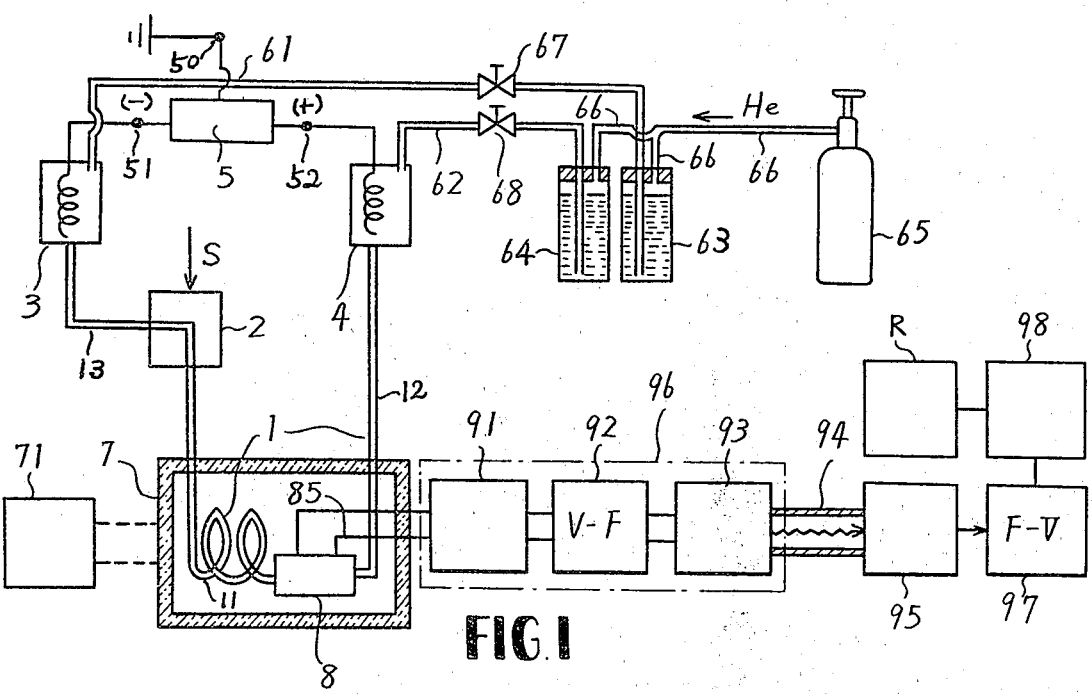
FIG. 1 is a schematic representation of an electrophoresis analyzer system according to the present invention, in which some portions of it is shown in section, with a circuit diagram.

Referring first to FIG. 1. There is shown a capillary tube 1, which is composed of three portions 11, 12 and 13, for an isotachophoretic column with an injection system 2. The tube 1 is connected to the current stabilized high voltage power supply 5 for providing an adjustable constant direct current, through a leading electrode compartment 3 and a terminal electrode compartment 4.

The power supply 5 has a transformer, a centre tap 50 with an out coil which is grounded, and polarity of the output can be reversed.

The compartments 3 and 4 are respectively connected to a first tube 61 and a second tube 62 which are deeply inserted into a leading electrolyte tank 63 and a terminal electrolyte tank 64. The tops of each of the tanks 63 and 64 are connected to a pressurized source of inert gas 65 e.g. He by tubing 66. Tubes 61 and 62 are provided with stop valves 67 and 68 for controling the liquid flow for the compartment 3 and 4 from the tank 63 and 64.

The tubes, 1, 61, 62 and 66, the port or the sample injection system 2, the compartments 3, 4, the tanks 63, 64 and valves 67, 68 are composed of a chemically stable insulating materials such as PTFE (Trade Mark: Teflon).

The column tube 1 has, for example, 100 cm length, 0.5 mm inner diameter and 2 mm outer diameter; the greatest part of the capillary tube 1 is placed in a bath 7 having a thermostat with a regulating power supply 71.

The system for measuring of zone boundaries is preferably composed of: a sensing cell 8, which is preferably formed as a gradient detector hereinafter described, situated near the end of the capillary tube 1; an impedance converter 91 with ultra-high input impedance and lower output impedance, connected to the output terminal of the sensing cell 8 by a PTFE sleeved wire 85 through the wall of the bath 7 with thermostat; a voltage to frequency converter 92 for generating a pulse signal whose frequency is proportional to the output voltage from the converter 91; signal transmission system T for electromagnetic or ultrasonic waves which is preferably composed of a radiation or luminescent source 93 such as photo-diode for generating an optical signal in response to the output signal of the converter 92, an optical transmitting channel 94 and a photo-electric converter 95 such as a photo-transistor or phototube for generating an electrical signal in response to the light signal from the source 93; insulating means 96 for isolating the potential of the circuit 91, 92 from ground to maintain the potential of the circuit 91, 92, 93 nearly equal to that of the sensing cell 8, for preventing any current leakage between each sensing electrode and the ground; a frequency to voltage converter 97 for generating the electrical signal proportional to the frequency of the output pulse from the sensor 95; a signal processing circuit 98 including a differential circuit for generating the signal representing the zone boundaries of separated ions; a recorder R having a constant chart speed for recording a electropherogram.

Also the aforementioned signal transmission system may be some other systems capable of insulating a detector from a recorder, and converters 92, 97 may be a frequency modulator and its demodulator.

Figure 2:
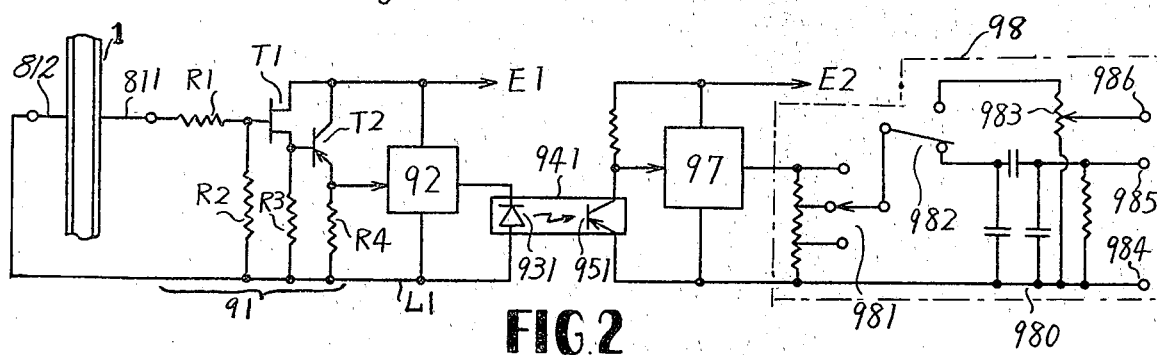
FIG. 2 represents a preferred embodiment of a measuring circuit of zone boundaries.

Referring to FIG. 2, the output terminals of a pair of sensing electrode 811, 812 are connected to the gate terminal of a field effect transistor T1 through an input resistor R1 of ultra high resistance, for example $10^9 - 10^{10}$ ohms and to the line L1 (not grounded) respectively. The gate of the transistor T1 and line L1 are connected by a second ultra high resistance resistor R2. A source terminal of the transistor T1 is connected to the line L1 by a resistor R3, and to the base terminal of the transistor T2 with an emitter-follower connection. The emitter of the transistor T2 is connected to the voltage-frequency converter 92 used for energizing a diode 931. A power supply E1 for the circuit 91 and 92 is preferably composed of an insulated transformer having very little leakage current or an electric cell or a battery. The aforesaid signal transmission system is composed of an optical radiation source of a diode 931, an opaque resin tube 941 and a phototransistor 951.

Besides the signal transmission system may be composed of, for example, radio wave or infrared, ultraviolet, radient rays transmitter means and their receivers.

A circuit 98 is for example composed of a range selector 981, a switch for selecting a potentiometer 983 or a differentiator 980.

Figure 3:
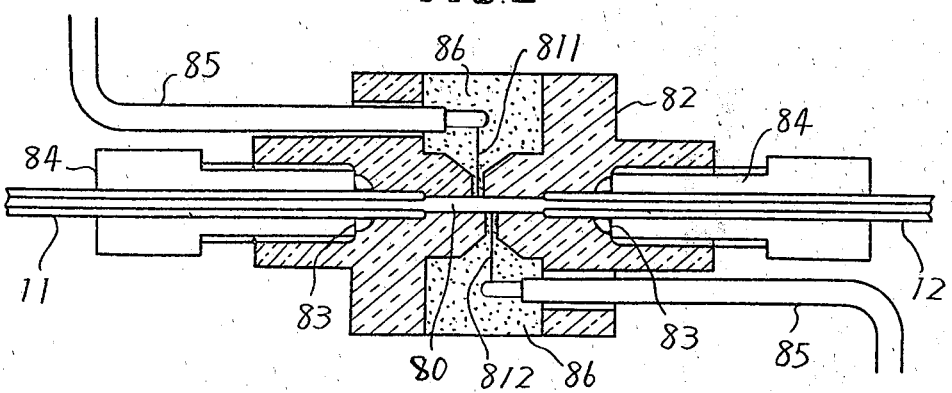
FIG. 3 shows a sectional view of a potential gradient detector preferably used in the present invention.

Referring to FIG. 3, the sensing cell 8 comprises mainly a capillary channel 80 formed between the capillary tubes 11 and 12 inserted tightly into a methacrylic resin block member 82 and a pair of sensing electrodes 811, 812 of Pt wire threaded tightly through the block normal to the axis of the channel 80, wherein both electrodes are separated by a small distance along the channel.

There are seals 83 of PTFE seal tapes between the tubes 11, 12 and the block 82; the fitting plugs 84 screwed in the block 82 press the seals 83 and support the tube 11 and 12. The other ends of the electrodes 811, 812 are soldered to each of the bare ends of the cable wires 85 threaded through the block 82 and fixed with Araldite (Trade Mark of CIBA) resin 86.

It is preferable that the diameter of the channel 80 is somewhat larger than the inner diameter of the tube 11, 12 and the electrodes 811, 812 are formed as thin as possible (for example: 0.08 mm of diameter) and the ends of the electrode 811, 812 are sized to just agree with the wall of the channel 80; so that there is a minimum chance of discharging ions moving in the sensing cell 8, so that bubble formation at the electrodes can be suppressed to some extent.

Figure 4:
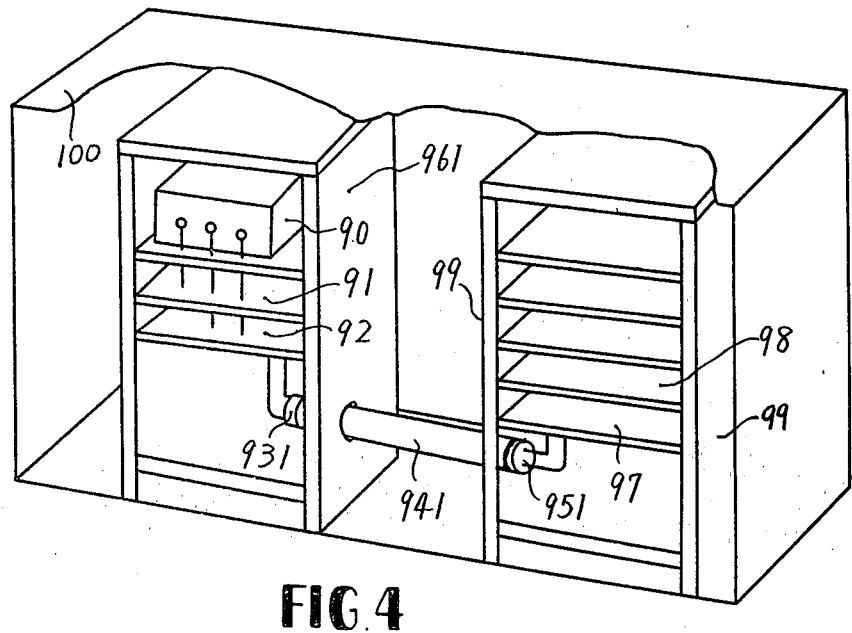
FIG. 4 is a perspective view of one embodiment of the arrangement of a measuring circuit.

In FIG. 4 there is shown an embodiment of the arrangement of the measuring circuit, wherein a case 961 of high insulation material such as methacrylic resin contains the impedance maching circuit 91, the voltage to frequency converter 92 and a power supply 90 for the circuit 91, 92. A power supply 90 is preferably composed of an electric cell or a battery, which is convenient for isolating the circuit 92 and 92 from the ground without a special insulated transformer.

The output terminals of the circuit 92 are connected to a photodiode 931 mounted in one end of the opaque tube 941 of high insulation material. The tube 941 is extended through the case 91 and a second case 99 containing the circuit 97, 98 etc. In the other end of the tube 941 there is mounted a photocell or a phototransistor 951, the output terminals of which are connected to the input terminals of the frequency to voltage converter 97. Numerals 984, 985, 986 are the output terminals of the circuit 98 to the recorder R.

Figures 5A, 5B:
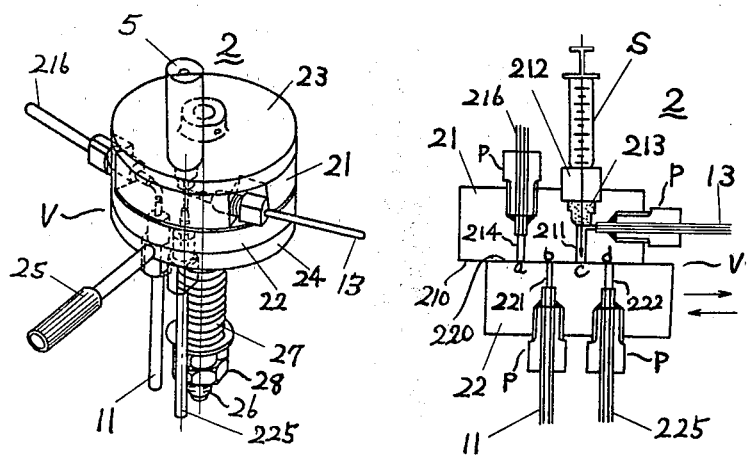
FIG. 5A and FIG. 5B show a partly schematic, vertical, sectional view of a sampling valve for introducing a sample between the leading and the terminal electrolytes and a perspective view of a practical embodiment.

Referring to FIG. 5A and 5B there are shown embodiments of a sample injection system 2 with a sampling valve V suitable for introducing a sample just on the boundary surface between the leading and the terminal electrolytes.

The valve as shown in FIG. 5A is simplified for explanation of operation and comprises a pair of valve members formed as a disc-shaped stationary PTFE valve member 21 and a disc-shaped movable PTFE valve member 22 which have smooth plain contact surfaces 210 and 220.

The valve member 22 has a channel 221 connected to a capillary tube 11 and a channel 222 connected to a first drain tank (not shown) with a tubing 225.

The valve member 21 has a first channel 211 communicating with a syringe needle guide 212 through a septum 213 and a second channel 214. The channel 214 is connected to a second drain tank (not shown) with a tubing 216. The first channel 211 is further connected to a tubing 11 to the leading electrode compartment 3. Besides, the valve is so constituted that it has three positions of valve operation; a first position for filling the capillary tubes 11, 12 and 13 with a leading electrolyte and a terminal electrolyte, a port $a$ to coincide with a port $b$ and a port $c$ to coincide with a port $d$; in the second position, which is shown in FIG. 5A, for preliminary injection of a sample, there is no communication among the ports $a$, $b$, $c$, and $d$; in the third position port $b$ and port $c$ communicate each other, for introducing a sample on the boundary surface of the both electrolytes. For these purposes, a line $ab$ and a line $cd$ are arranged parallel to a direction of sliding of a movable valve member 22 and a length of $ab$ is equal to that of $cb$.

Fig. 5B shows the embodiment of sampling valve 2 which is convenient for practical use, which comprises a stationary valve member 21 mounted to a stationary steel disk 23 and a rotatory valve member 22 mounted to a rotating steel disc 24. A disc 24 has a rotation handle 25, a shaft 26, a pressurizing spring 27 placed between the steel disc 24 and a nut 28. The general constructions of the valve and operation is substantially the same as the embodiment of FIG. 5A.

In operation prior to measuring, the leading electrolyte and terminal electrolyte are charged in the capillary tube 1, then a sample is introduced between the both electrolytes.

In the first step, a movable disc 22 of the sampling valve V is placed in the first position wherein the port *a, c* communicate with the ports *b, d* respectively, and a valve 67 and a valve 68 are opened, then a terminal electrolyte in the tank 64 flows through a tubing 62, compartment 4, second portion 12 of a capillary tube 1, a sensing cell 8, a first portion 11 of the tube 1 and the port *b, a* of the valve V and a tubing 216 to a drain tank; a leading electrolyte in the tank 63 flows through a tubing 61, a leading electrode compartment 3, a thrid portion 13 of the capillary tube 1, the ports *c* and *d* and a tubing 225 to the drain tank.

In the second step the valve is operated to the second position as shown in FIG. 5A, and a sample in the mircoliter syringe S is injected gently into the channel 211 through a syringe needle inserted into the channel 211 from the septum 23 to the vicinity of a port *c*, then the sample injected located the channel adjacent to the port *c* with the result that the terminal electrolyte in the tube 13 is slightly pushed back for the leading electrolyte tank 64, to give place to an injected sample.

Thus a boundary is formed between the terminal electrolyte and the sample solution.

In the third step, the valve is operated to the third position wherein a port *b* coincides with a port *c*, so that the leading electrolyte comes in contact with the sample solution. Thus the sample introduction is completed just on the boundary between the leading and the terminal electrolytes.

The tanks 63, 64 then are cut off from the capillary tube 1 by the stop valves 67 and 68, in order to prevent electroendomosis in the capillary tube.

In the migration process, the power supply is put on to start the migration in the capillary tube in the constant temperature bath 7. In the course of migration, for example, each ion with a negative charge migrates for the leading electrode with positive potential according to its mobility, and ions in the sample solution are separated into a series of layer deposited in order of their mobilities.

In the final aspect, as shown in FIG. 6A, 6B, 6C where separation is finished, each zone contains a single sort of ions respectively and migrate at a same speed and a (concentration) density of ions in any zone, for example of the C$^-$ ions, is given by the following equation (1).

$$Ca/Cc = (1 + Mr/Mc)/(1 + Mr/Ma) \quad (1)$$

Where
- $Ca$: (concentration) density of leading ions
- $Cc$: (concentration) density of C$^-$ ions in the zone
- $Mr$: mobility of positive ions The equation teaches that a density of ions in each completely separated zone has a value independent of the numbers of ions in each zone.

Thus the width of each zone of same ions is proportional to the numbers of ions. FIG. 6D shows an electropherogram recorded as a differential of the output from the potential gradient detector 8. Namely in FIG. 1 a gradient detector 8 generates an output voltage proportional to the potential difference between both sensing electrodes 811, and 812, which is introduced to the voltage to frequency converter 92 through the impedance converter 91.

The converter 93 receiving a pulse signal from the converter 92 generates a radiant energy signal, for example, optical radiation of a diode 931 of the same frequency as the output from the converter 92. The converter 95 (a photocell 951) generates an electric signal in response to the signal transmitting on the path 94 and supplies it to a frequency to voltage converter 97. Thus the converter 97 regenerates an electric signal proportional to the output voltage of the detector 8, without electric potential coupling between them.

The output of the converter 97 is supplied to the recorder R through a range selector 981, a switch 982 or either a differentiating circuit 980 or a potentiometer 983. Thus the recorder writes either a potential gradient curve or a differential curve of the output in a wide range.

Also circuit 98 may be varied so as to enable the recorder to record both curves at the same time.

EXAMPLE I

In the embodiment of FIG. 1, the terminal electrode compartment 3 and the injection port 2 were connected with PTFE tube (inner diameter: 1 mm, outer diameter: 3 mm, length: 10 cm), the injection port 2 and the leading electrolyte compartment 4 were connected with a PTFE capillary tube of 0.5 mm inner diameter, 2 mm outer diameter and 1 mm length.

Then an aqueous solution of 0.01M histidine and 0.01M histidine HCl as the leading electrolye, and an aqueous solution of 0.01M L-glutamic acid as the terminal electrolyte are charged in the tank 63 and 64 respectively.

Then 5 μl mixture of 0.01M sodium sulphate, 0.01M sodium nitrate, 0.01M sodium oxalate, 0.01M sodium formate, 0.01M sodium citrate, 0.01M sodium maleinate, 0.01M sodium acetate was sampled in a microliter syringe.

Then the sample was introduced just on the boundary surface of the both electrolyte, as hereinbefore described, then migration was performed with migration current of 250 μA.

A temperature of the bath 7 was kept at 20°C during the migration procedures. It was found that no bubbles were generated on the sensing electrodes even at 250 uA migration current. The result obtain through a differential circuit 980 in given in FIG. 7B, which shows that the boundary were detected with sufficient stability.

EXAMPLE II

Figure 7B:
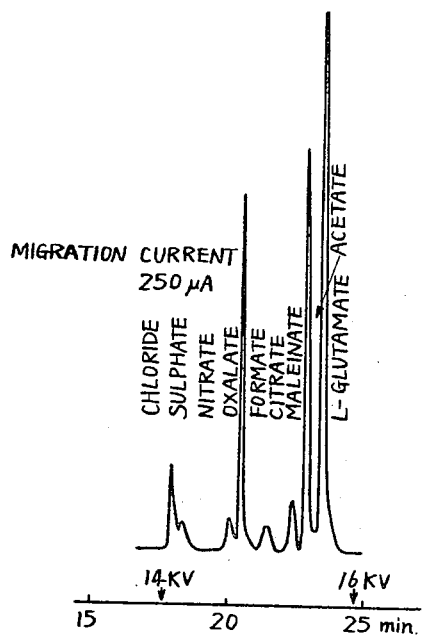
FIGS. 7A, 7B, FIG. 8A to FIG. 8C illustrate some electropherograms obtained with use of an analyzer of the invention.
Figure 7A:
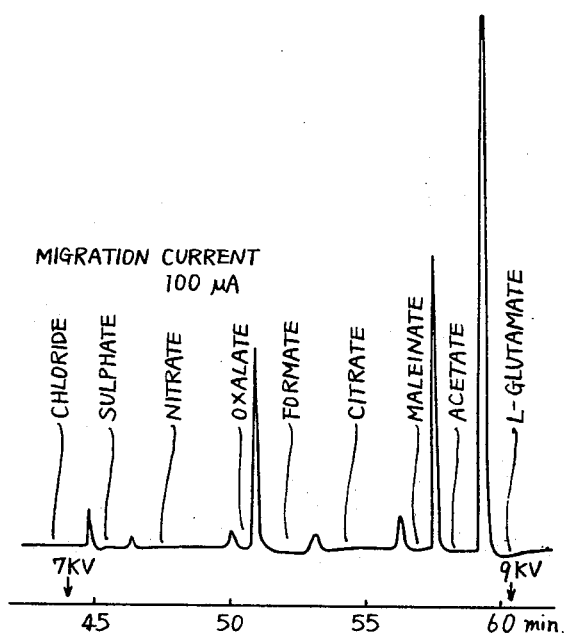

FIG. 7A shows the electrophoregram obtained with the same sample and same operating condition as that of Example I, except that the migration current is 100 μA and the attenuation rate by a range selecter 981 is half of Example I.

This electropherogram shows a good resolution of the detector. In detail FIG. 7A shows that the zone boundary between sulphate and nitrate having mobility difference of about 10 percent and diffusion coefficient of $10^5$ cm$^2$/sec. can be detected as a peak of 180 uV height, with a noise level of 10 uV, but without any discernible baseline drift. If the peak several times as high as the level of the noise is assumed to be the detection limit, this potential gradient detector can be said to detect the boundary between two zones having a mobility difference of about 1 percent, in case of samples having diffusion coefficient of $10^5$ cm$^2$/sec.

EXAMPLE III

Several experiments were performed to test the separation to trace quantity of samples. Migration was done for several quantities of samples with 100 μA of migration current. The thermo-bath temperature was kept at 20°C.

Figures 8A, 8B, 8C:
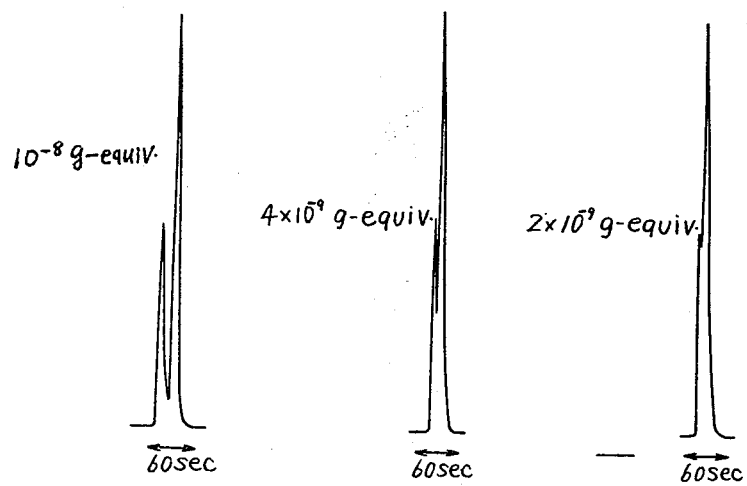

FIGS. 8A, 8B and 8C illustrate the electropherograms recorded on the recorder R through the differential circuit 980, for the adipic acid of $10^{-8}$ gram equivalent, $4\times10^{-9}$ gram equivalent and $2\times10^{-9}$ gram equivalent, using the solution of 0.01M histidine and 0.01M histidine HC1 as a leading electrolyte, and the solution of 0.01M glutamic acid as a terminal electrolyte. These results shows the minimum sample size to detect two adjacent boundaries, as peaks, is approximately $2\times10^{-9}$ gram equivalent.

EXAMPLE IV

After about 200 hours' operation at 100 μA of migration current, at 20°C of the bath temperature with the same sample as in FIG. 7A, 7B, the sensitivity and the noise level remained at the almost same level as the electropherograms in FIG. 7A, 7B.

As shown hereinbefore this invention has various advantages, for instance.

1. Through isolation of the sensing cell, which is situated at a high voltage to ground, from the ground potential, by converting the electrical signal provided by the sensing cell into an optical signal, reduction of the current between the sensing electrodes and ground is attained.
2. Through scraping off the projecting parts of the sensing electrodes, reduction of the electric current between the two sensing electrodes is further attained.
3. Through expanding the cross-sectional area of the cell, reduction of the current density in the sensing cell is further attained.
4. As a result of each abovementioned improvement of their co-operation, generation of bubbles in the sensing cell was suppressed or prevented and it is possible to perform stable measurement of zone boundaries up to a high migration current.
5. As a result of (4), good resolution and sensitivity can be obtained.
6. As a result of (4), migration process can be finished in a shorter time.

Although the invention has been described in its preferred form with a certain degree of particulality, it is understood that the present disclosure of the preferred form may be changed in details of construction and the combination and arrangement of parts may be resorted to without departing from the spirit and scope of the invention as hereafter claimed.

What we claim is:

1. An electrophoretic measurement system comprising: an electrophoretic column means (11, 12, 13); sample introducing means for introducing a sample into said column means, power means (5) for generating a potential gradient along said column means; detector means (8) for sensing zone boundaries produced within said column means and providing an electrical output signal; signal transmitter means (93) for receiving the output electrical signal from said detector means and transmit it as a wave; converter means (95) disposed for receiving said wave and generating an electrical signal in response to said transmitted wave; reading means for reading the output signal from said converter means.

2. The system of claim 1, wherein said transmitter means comprises a source of optical radiation and an optical path and said converter means comprises a photoelectric sensor.

3. The system of claim 2, wherein said source of optical radiation is composed of a semiconductor diode.

4. The system of claim 1, wherein said detector means is a gradient detector for sensing a potential gradient within liquid in said column tube.

5. The system of claim 4, wherein said detector means comprises a channel with a wall, which communicates to said column means and electrodes disposed apart from each other.

6. The system of claim 4, wherein said detector electrodes comprises a pair of thin electrodes plugged, in the wall of said channel, without projecting into the inside from the inner surface of the wall.

7. The system of claim 4, further including a detector output terminal and a transmitter input terminal, an impedance converter, which has a high input impedance and a lower output impedance, interposed between the output terminal of the detector means and the input terminal of said transmitter means.

8. The system of claim 4, further including: means for generating a pulse signal of the frequency related to the output from said detector means to pulsate the input signal to said transmitter means; means for generating an electrical signal interposed between said converter means and said reading means.

9. An electrophoretic measurement system comprising in combination
   a. a tube (1) for defining an isotachophoretic column therein said tube (1) having central, leading and terminal portions (11, 12, 13);
   b. at least first and second tanks (63, 64) for holding leading and terminal electrolytes connected to said leading and terminal portions;
   c. power supply means connected to said tube disposed to apply a current across said central portion to carry out electrophoretic separation therein;
   d. a bath tank for holding said tube central portion;
   e. valve means (2) connected to said tube (1) having first and second positions allowing selective coupling to said leading and terminal electrolytes and a third position allowing feeding of a sample to said tube (1);
   f. sensing means connected to said central portion including a capillary channel (80) and first and second sensing electrodes (811, 812) disposed on said column means, and electrical units measuring circuitry fed by said sensing electrodes;
   g. transmitter means coupled to said sensing means converting the output therefrom to a wave signal;
   h. converter means disposed to receive said wave signal and convert said wave signal to an electrical signal; and,
   i. reading means coupled to said converter means for displaying the output therefrom.

10. The system of claim 9, wherein said transmitter means comprises a source of optical radiation and an optical path and said converter means comprises a photoelectric sensor.

11. The system of claim 10, wherein said source of optical radiation is composed of a semiconductor diode.

12. The system of claim 9 wherein said valve means includes a stationary disc (21) and a rotating disc (22)

said discs having smooth contact surfaces and being in contact one with the other, first and second channels (211,214) on said stationary disc, first and second channels (221, 222) on said movable disc, and connecting tubing connecting certain channels to said first and second tands (63, 64) and tube portions (11, 12, 13), sample injection means in one of said discs and means to turn said rotatable disc with respect to said stationary disc so that said first and second channels in one disc may separately be disposed opposite one, the other or neither of said first and second channels in the other disc so that a sample may be injected through said sample injection means between a leading and terminal electrolyte fed to said defined isotachophoretic column by said valve means across said channels.

13. The system of claim 1, wherein the signal transmission line from the output terminals of said detector means to said signal transmitter means is insulated from the ground.

14. The system of claim 1, wherein the signal differentiating means is interposed between said converter means and said reading means.

* * * * *